US010125064B2

(12) United States Patent
Laroche et al.

(10) Patent No.: US 10,125,064 B2
(45) Date of Patent: Nov. 13, 2018

(54) METHOD FOR SEPARATING META-XYLENE USING A ZEOLITIC ADSORBENT WITH A LARGE EXTERNAL SURFACE AREA

(71) Applicants: IFP ENERGIES NOUVELLES, Rueil-Malmaison (FR); CECA S.A., La Garenne Colombes (FR)

(72) Inventors: Catherine Laroche, Vernaison (FR); Philibert Leflaive, Mions (FR); Arnaud Baudot, Vernaison (FR); Ludivine Bouvier, Orthez (FR); Cecile Lutz, Gan (FR); Serge Nicolas, Lons (FR)

(73) Assignees: IFP ENERGIES NOUVELLES, La Garenne Colombes (FR); ARKEMA FRANCE, Colombes (FR)

( * ) Notice: Subject to any disclaimer, the term of this patent is extended or adjusted under 35 U.S.C. 154(b) by 0 days.

(21) Appl. No.: 15/501,688

(22) PCT Filed: Aug. 4, 2015

(86) PCT No.: PCT/EP2015/067966
§ 371 (c)(1),
(2) Date: Feb. 3, 2017

(87) PCT Pub. No.: WO2016/020386
PCT Pub. Date: Feb. 11, 2016

(65) Prior Publication Data
US 2017/0226031 A1 Aug. 10, 2017

(30) Foreign Application Priority Data
Aug. 5, 2014 (FR) .................................... 14 57623

(51) Int. Cl.
*C07C 7/13* (2006.01)
*B01J 20/18* (2006.01)
*B01J 20/28* (2006.01)

(52) U.S. Cl.
CPC ................. *C07C 7/13* (2013.01); *B01J 20/18* (2013.01); *B01J 20/28059* (2013.01); *B01J 20/28061* (2013.01); *B01J 20/28071* (2013.01); *B01J 20/28073* (2013.01); *B01J 20/28083* (2013.01)

(58) Field of Classification Search
None
See application file for complete search history.

(56) References Cited

U.S. PATENT DOCUMENTS

| 2,985,859 | A | | 5/1961 | Broughton et al. |
| 4,247,987 | A | * | 2/1981 | Coulaloglou ............. B01J 8/42 34/249 |
| 4,306,107 | A | | 12/1981 | Broughton |
| 4,326,092 | A | | 4/1982 | Neuzil |
| 4,617,282 | A | * | 10/1986 | van der Vleugel .... B01J 20/183 252/62.51 R |
| 5,382,747 | A | | 1/1995 | Kulprathipanja |
| 5,900,523 | A | | 5/1999 | Kulprathipanja |
| 6,057,487 | A | * | 5/2000 | Munson .................... C07C 7/13 585/814 |
| 6,180,550 | B1 | * | 1/2001 | Beck ........................ B01J 29/04 502/60 |
| 7,718,842 | B2 | | 5/2010 | Leflaive et al. |
| 7,728,187 | B2 | | 6/2010 | Kulprathipanja et al. |
| 7,785,563 | B2 | | 8/2010 | Ryoo et al. |
| 2007/0038012 | A1 | | 2/2007 | Feflaive |
| 2009/0326310 | A1 | | 12/2009 | Kulprathipanja et al. |
| 2015/0057481 | A1 | | 2/2015 | Chaumonnot et al. |
| 2015/0246860 | A1 | * | 9/2015 | Bender ................... C07C 6/123 585/303 |
| 2016/0009614 | A1 | | 1/2016 | LaRoche et al. |
| 2016/0207025 | A1 | * | 7/2016 | Laroche ............ B01J 20/28059 |
| 2017/0304799 | A1 | * | 10/2017 | Bouvier ................ B01J 20/186 |

FOREIGN PATENT DOCUMENTS

| CN | 103214003 A | 7/2013 |
| FR | 2889698 A | 2/2007 |
| FR | 2889699 A1 | 2/2007 |
| FR | 2988718 A1 | 10/2013 |
| FR | 3002461 A1 | 8/2014 |
| JP | 069438 A | 1/1994 |
| WO | 2007043731 A1 | 4/2007 |
| WO | 2013106816 A1 | 7/2013 |

OTHER PUBLICATIONS

International Search Report and Written Opinion for International Application No. PCT/EP2015/067966, dated Oct. 12, 2015, 11 Pages.
E.P. Barrett et al., "The Determination of Pore Volume and Area Distributions in Porous Substances. I. Computations from Nitrogen Isotherms", J. Am. Chem. Soc., vol. 73, No. 1, (1951) pp. 373-380.
D. Verboekend et al., "Hierarchical Y and USY Zeolites Designed by Post-Synthetic Strategies", Adv., Funct. Mater. 22, 2012, pp. 916-928.

* cited by examiner

*Primary Examiner* — Tam M Nguyen
(74) *Attorney, Agent, or Firm* — RatnerPrestia

(57) ABSTRACT

The invention relates to a method for separating meta-xylene from C8 aromatic fractions, using a zeolitic adsorbent based on sodium-exchanged or sodium-and-lithium-exchanged agglomerated crystals of zeolite Y, with a large external surface area.

26 Claims, 2 Drawing Sheets

METHOD FOR SEPARATING META-XYLENE USING A ZEOLITIC ADSORBENT WITH A LARGE EXTERNAL SURFACE AREA

CROSS-REFERENCE TO RELATED APPLICATIONS

This is the national phase of International Application No. PCT/EP2015/067966, filed 4 Aug. 2015, which claims priority to French Application No. 1457623, filed 5 Aug. 2014. The disclosure of each of these applications is incorporated herein by reference in its entirety for all purposes.

FIELD OF THE INVENTION

The invention relates to a process for separating meta-xylene from its isomers present in a gaseous or liquid mixture, using an adsorbent in agglomerate form comprising faujasite zeolite (FAU) of NaY type and/or of NaLiY type and having a large external surface area, said external surface area being characterized by a mesopore population determined by nitrogen adsorption measurement. The process of the present invention allows the production of meta-xylene of very high purity.

BACKGROUND OF THE INVENTION

The use of zeolite adsorbents containing zeolites of NaY and/or NaLiY type for selectively adsorbing meta-xylene in a mixture of aromatic hydrocarbons is well known in the prior art.

For example, U.S. Pat. No. 4,306,107, U.S. Pat. No. 4,326,092, U.S. Pat. No. 5,382,747, U.S. Pat. No. 5,900,523 and U.S. Pat. No. 7,728,187 and also FR 2 889 698 and FR 2 889 699 show that zeolite adsorbents comprising aluminosilicates based on sodium or based on sodium and lithium are effective for separating out the meta-xylene present in aromatic C8 fractions (fractions comprising aromatic hydrocarbons containing 8 carbon atoms).

The adsorbents described in U.S. Pat. No. 5,900,523 are used as adsorption agents in liquid-phase processes, preferably of simulated counter-current type, similar to those described in U.S. Pat. No. 2,985,589 and which apply, inter alia, to aromatic C8 fractions.

In the patents listed above, the zeolite adsorbents are present in the form of crystals in powder form or in the form of agglomerates predominantly formed from zeolite powder and up to 20% by weight of inert binder.

The synthesis of FAU zeolites is usually performed by nucleation and crystallization of silico-aluminate gels. This synthesis leads to crystals (generally in powder form), which are particularly difficult to use on an industrial scale (substantial losses of feedstocks during the manipulations). It is thus preferred to use the agglomerated forms of these crystals, in the form of grains, strands and other agglomerates, these said forms possibly being obtained by extrusion, pelletizing, atomization and other agglomeration techniques known to those skilled in the art. These agglomerates do not have the drawbacks inherent in pulverulent materials.

Moreover, zeolite crystals are usually prepared from aqueous sodium solutions (for example aqueous sodium hydroxide solution), and, if so desired, the sodium cations may be totally or partly replaced (exchanged) with other cations, for example lithium. These cation exchanges may be performed before and/or after agglomeration of the pulverulent zeolite with the agglomeration binder, according to standard techniques known to those skilled in the art.

The agglomerates, whether in the form of platelets, beads, extrudates or the like, are generally formed from zeolite crystals, which constitute the active component (as regards adsorption) and an agglomeration binder. This agglomeration binder is intended to ensure the cohesion of the crystals with each other in the agglomerated structure, but must also be able to ensure sufficient mechanical strength for said agglomerates so as to avoid, or at the very least to minimize, the risks of fracturing, breaking or cracking that might arise during their industrial use during which the agglomerates are subjected to numerous stresses, such as vibrations, large and/or frequent pressure variations, movements and the like.

The preparation of these agglomerates is performed, for example, by slurrying zeolite crystals in powder form with a clayey paste, in proportions of the order of 80% to 90% by weight of zeolite powder per 20% to 10% by weight of binder, followed by forming into beads, platelets or extrudates, and heat treatment at high temperature to bake the clay and to reactivate the zeolite, the cation exchange(s), for instance the total or partial exchange with lithium, possibly being performed before and/or after agglomeration of the pulverulent zeolite with the binder.

Zeolite substances are obtained, the particle size of which is a few millimeters, or even of the order of a millimeter, and which, if the choice of the agglomeration binder and the granulation are performed in a standard manner, have a satisfactory set of properties, in particular of porosity, mechanical strength, abrasion resistance, and the like. However, the adsorption properties of these agglomerates are obviously reduced relative to the starting active powder on account of the presence of agglomeration binder which is inert with respect to adsorption.

Various means have already been proposed for overcoming this drawback of the agglomeration binder being inert as regards the adsorption performance, among which is the transformation of all or of at least some of the agglomeration binder into zeolite that is active as regards adsorption. This operation is now well known to those skilled in the art, for example under the name "zeolitization". To perform this operation, zeolitizable binders are used, usually belonging to the kaolinite family, and preferably calcined beforehand at temperatures generally between 500° C. and 700° C.

U.S. Pat. No. 4,306,107 describes the use, as a selective adsorbent for meta-xylene, of a zeolite Y, in which the exchangeable cationic sites are occupied by sodium atoms. To obtain satisfactory selectivity in favor of meta-xylene, it is recommended to use a partially hydrated zeolite which has a loss on ignition at 950° C. of from 2% to 7% by weight relative to the initial weight of the adsorbent. Said document recommends separation via a simulated moving bed process at a temperature between 20° C. and 250° C. and at a pressure between atmospheric pressure and 3.5 MPa (35 bar), this value being chosen so as to keep the feedstock in liquid form. The chosen desorbent is toluene. Occupation of the exchangeable sites of the zeolite with sodium ions and activation so as to obtain the desired loss on ignition make it possible to obtain agglomerates which have, from the point of view of adsorption of the meta-xylene contained in aromatic C8 fractions, improved capacity and selectivity properties.

Besides a high adsorption capacity and good selectivity properties toward the species to be separated from the reaction mixture, the adsorbent must have good matter transfer properties so as to ensure a sufficient number of theoretical plates to achieve efficient separation of the species in the mixture, as indicated by Ruthven in the book entitled "*Principles of Adsorption and Adsorption Processes*", John Wiley & Sons, (1984), pages 326 and 407. Ruthven indicates (ibid., page 243), that, in the case of an agglomerated adsorbent, the overall matter transfer depends on the addition of the intra-crystalline diffusional resistance and the inter-crystalline diffusional resistance.

The intra-crystalline diffusional resistance is proportional to the square of the diameters of the crystals and inversely proportional to the intra-crystalline diffusivity of the molecules to be separated.

The inter-crystalline diffusional resistance (also known as the "micropore resistance") is, itself, proportional to the square the diameters of the agglomerates, inversely proportional to the porosity contained in the macropores and mesopores (i.e. the pores whose diameter is greater than 2 nm) in the agglomerate, and inversely proportional to the diffusivity of the molecules to be separated in this porosity.

The size of the agglomerated adsorbents is an important parameter during the use of the adsorbent in industrial application, since it determines the loss of feedstock in the industrial unit and the uniformity of filling. The particle size distribution of the agglomerates must thus be narrow, and centered on number-mean diameters typically between 0.40 mm and 0.65 mm so as to avoid excessive losses of feedstock. The porosity contained in the macropores and mesopores does not participate in the adsorption capacity. Consequently, a person skilled in the art will not seek to increase it for the purpose of reducing the macropore diffusional resistance, given that this would take place at the expense of the volume-based adsorption capacity.

To estimate the improvement in the transfer kinetics, use may be made of the plate theory described by Ruthven in "*Principles of Adsorption and Adsorption Processes*", ibid., pages 248-250. This approach is based on the representation of a column by a finite number of ideally stirred hypothetical reactors (theoretical stages). The equivalent height of theoretical plates is a direct measurement of the axial dispersion and of the resistance to matter transfer of the system.

For a given zeolite structure, a given size of adsorbent and a given operating temperature, the diffusivities are fixed, and one of the means for improving the matter transfer consists in reducing the diameter of the crystals. A gain in the overall transfer will thus be obtained by reducing the size of the crystals.

A person skilled in the art will thus seek to minimize the diameter of the zeolite crystals in order to improve the matter transfer.

U.S. Pat. No. 7,728,187 thus claims a process for separating meta-xylene from a mixture of aromatic C8 hydrocarbons which consists in placing the mixture in contact, under adsorption conditions, with an adsorbent, in which the crystals of zeolite Y exchanged with sodium are between 0.05 µm and 0.7 µm in size, so as to improve the matter transfer performance.

The Applicant has nevertheless observed that the synthesis, filtration, manipulation and agglomeration of zeolite crystals which are less than 0.7 µm in size involve cumbersome, sparingly economic processes which are thus difficult to industrialize. In addition, such adsorbents comprising crystals less than 0.7 µm in size also prove to be more fragile, and it then becomes necessary to increase the content of agglomeration binder in order to reinforce the cohesion of the crystals with each other in the agglomerate.

However, increasing the content of agglomeration binder leads to densification of the agglomerates, which is the cause of an increase in the macropore diffusional resistance. Thus, despite a reduced intra-crystalline diffusional resistance due to the decrease in the size of the crystals, the increase in the macropore diffusional resistance on account of the densification of the agglomerate does not allow an improvement in the overall matter transfer. In the context of the present invention, the term "agglomerate" may be used in place of the term "adsorbent" and should be understood as defining the same object.

There is consequently still a need for zeolite adsorbent materials prepared from zeolite of FAU type that are easily manipulable at the industrial level, i.e. whose constituent crystals are advantageously greater than 0.7 µm in size, but having an improved overall matter transfer relative to that of an adsorbent prepared from conventional zeolite crystals of FAU type of identical size (i.e. greater than 0.7 µm), while at the same time conserving high adsorption capacity.

Such zeolite adsorbent materials based on zeolite of FAU type, and in particular containing zeolites of NaY and/or NaLiY type, might provide significant improvements to processes for separating xylenes present in the form of mixtures of isomers in aromatic C8 hydrocarbon fractions, and in particular might greatly improve the selective adsorption of meta-xylene in mixtures of aromatic C8 hydrocarbons.

SUMMARY OF THE INVENTION

A first object of the present invention is thus to propose a process for separating meta-xylene from aromatic C8 fractions, in the gas phase or in the liquid phase, using a zeolite adsorbent in the form of agglomerates with optimized properties. The zeolite adsorbent used in the process according to the invention especially has maximum properties of selectivity toward meta-xylene and of matter transfer, while at the same time having high mechanical strength and high adsorption capacity. The process according to the invention is preferably a process for separating meta-xylene in the liquid phase, preferably a process for separating meta-xylene in the liquid phase of simulated counter-current type.

Figure 1:
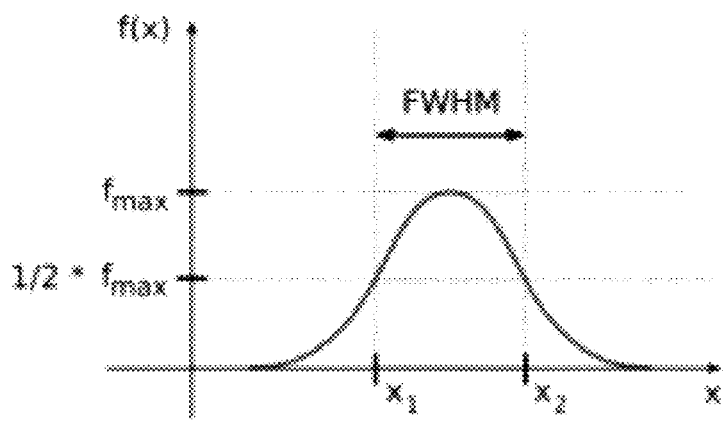
FIG. 1: plot showing the full width at half maximum (FWHM) of the volume distribution dV/dDm.

More precisely, the present invention relates to a process for separating meta-xylene using a zeolite adsorbent comprising at least one faujasite-type zeolite Y comprising sodium or sodium and lithium, in which process the external surface area of said zeolite adsorbent, measured by nitrogen adsorption, is greater than 40 $m^2 \cdot g^{-1}$, preferably greater than 50 $m^2 \cdot g^{-1}$, and more preferably between 60 $m^2 \cdot g^{-1}$ and 200 $m^2 \cdot g^{-1}$, and more preferentially between 80 $m^2 \cdot g^{-1}$ and 200 $m^2 \cdot g^{-1}$, and even more preferably between 100 $m^2 \cdot g^{-1}$ and 200 $m^2 \cdot g^{-1}$, said external surface area being associated with a population of mesopores with a mean diameter of between 2 nm and 50 nm. The term "associated" in the preceding sentence indicates that the population of mesopores contributes to the measured value of the external surface area, in addition to the external surface area of the zeolite crystals.

DETAILED DESCRIPTION OF CERTAIN EMBODIMENTS OF THE INVENTION

The mean diameter is determined via the Barrett-Joyner-Halenda method (BJH method, E. P. Barrett, L. G. Joyner, P. P. Halenda, "The Determination of Pore Volume and Area Distributions in Porous Substances. I. Computations form Nitrogen Isotherms", *J. Am. Chem. Soc.*, 73(1), (1951) 373-380), from the nitrogen adsorption isotherm at 77 K. Advantageously, the volume-mean diameter distribution thus determined, represented graphically by dV/dDm or dV/d log Dm as a function of the mean diameter Dm, corresponds to a narrow unimodal distribution.

In the text hereinbelow, and unless otherwise indicated, the limits of a range of values are included in that range, especially in the expressions "between" and "ranging from . . . to . . . ".

The term "unimodal distribution" means a distribution having only one peak. A unimodal mean diameter distribution is thus characterized by only one peak, for which the value of the mean diameter at the top of the peak is known as the "mode" or alternatively the dominant value, and represents the most frequent value of the distribution. Preferably, the mesopore population of said zeolite adsorbent has mean diameters at the mode of between 2 nm and 30 nm and preferably between 2 nm and 20 nm. When a distribution has two peaks separated by a trough, the distribution is said to be bimodal. The invention does not concern the case of bimodal or even multimodal distribution, i.e. distribution in which there are several zones of concentration of values separated by discontinuities. Such distributions are characteristic of the presence of several populations of pores with different mean diameters.

The term "narrow" used to characterize the mean diameter distribution of the mesopores, indicates that the full width at half maximum of the distribution about the mode is less than 20 nm, preferably less than 15 nm, preferably between 10 nm and 0.1 nm and more preferably between 5 nm and 0.5 nm, as described later in the characterization techniques.

The process according to the invention preferably uses a zeolite adsorbent preferably comprising at least one non-zeolite phase, at least a part of which is a clay or a mixture of clays used in the preparation method as agglomeration binder allowing cohesion between the crystals, derived from the synthesis, before being optionally totally or partially zeolitized, i.e. transformed into active zeolite for the adsorption of the molecules under consideration, i.e. preferentially converted into zeolite, preferably FAU zeolite, more preferably of Y type.

According to one embodiment of the invention, the zeolite adsorbent may have a lithium content of less than 8%, preferably between 0 and 4%, expressed as weight of lithium oxide $Li_2O$ relative to the total mass of the adsorbent.

According to another embodiment of the invention, the total content of alkali metal or alkaline-earth metal ions other than lithium and sodium is between 0 and 1%, this total content being expressed, respectively, as mass of lithium oxide $Li_2O$ and of sodium oxide $Na_2O$, relative to the total mass of the zeolite adsorbent.

Preferably, the zeolite adsorbent according to the present invention is a zeolite adsorbent comprising at least one faujasite-type zeolite Y, in other words an adsorbent based on FAU zeolite(s), generally referenced under the name FAU-type zeolite Y. The term "FAU-type zeolite Y" means a zeolite whose Si/Al atomic ratio is greater than 1.50, preferably between 1.60 and 6.00, preferably between 1.80 and 4.00 and even more preferably between 2.00 and 2.80.

According to a preferred embodiment, the process according to the invention uses a zeolite adsorbent comprising mesoporous crystals of zeolite Y. The term "mesoporous" refers to zeolite crystals which have, in combination with the microporosity inherent in the structure of zeolite, internal cavities of nanometric size (mesoporosity), which are readily identifiable by observation using a transmission electron microscope (TEM), as described, for example, in U.S. Pat. No. 7,785,563.

According to another embodiment, no zeolite structure other than the FAU structure is detected by x-ray diffraction (known to those skilled in the art by the abbreviation XRD) in the zeolite adsorbent used in the process of the present invention. The term "no" means less than 5% by mass, preferably less than 2% by mass, of zeolite of structure other than the FAU structure, relative to the total mass of the adsorbent, the mass fractions being determined by XRD.

According to yet another preferred embodiment, the process according to the invention uses a zeolite adsorbent whose mass fraction of FAU-type zeolite(s) Y is greater than or equal to 80% relative to the total weight of the adsorbent, the remainder to 100% preferably being formed from non-zeolite phase.

The process according to the invention uses an adsorbent that may contain a non-zeolite phase, i.e. a non-crystalline phase that is essentially inert with respect to adsorption. The mass fraction of zeolite(s) (degree of crystallinity of the adsorbent) may be determined by x-ray diffraction analysis, known to those skilled in the art by the abbreviation XRD, as indicated previously.

According to yet another preferred embodiment, the process according to the invention uses a zeolite adsorbent which has an Si/Al atomic ratio of between 1.50 and 6.50, preferably between 2.00 and 6.00, more preferably between 2.00 and 4.00 and even more preferably between 2.20 and 2.80.

According to a preferred embodiment, the process according to the invention uses a zeolite adsorbent which has a loss on ignition, measured at 950° C. according to standard NF EN 196-2, of less than or equal to 7%, preferably between 0 and 6%, preferably between 0 and 4%, more preferably between 0 and 3% and advantageously between 0 and 2.5%.

The process according to the invention preferably uses a zeolite adsorbent simultaneously comprising macropores, mesopores and micropores. The term "macropores" means pores whose diameter is greater than 50 nm, preferably between 50 nm and 400 nm. The term "mesopores" means pores whose diameter is between 2 nm and 50 nm, limits not included. The term "micropores" means pores whose diameter is less than 2 nm.

According to yet another preferred embodiment, the zeolite adsorbent of the present invention has a total volume contained in the macropores and mesopores (sum of the macropore volume and the mesopore volume), measured by mercury intrusion, advantageously between 0.20 $cm^3 \cdot g^{-1}$ and 0.70 $cm^3 \cdot g^{-1}$, preferably between 0.20 $cm^3 \cdot g^{-1}$ and 0.55 $cm^3 \cdot g^{-1}$ and very preferably between 0.20 $cm^3 \cdot g^{-1}$ and 0.50 $cm^3 \cdot g^{-1}$.

The ratio (macropore volume)/(macropore volume+mesopore volume) is preferably between 0.2 and 1, very preferably between 0.4 and 0.8 and even more preferably between 0.45 and 0.65.

In the context of the present invention, preference is also given to a process using a zeolite adsorbent whose micropore volume, evaluated by the t-plot method from the nitrogen ($N_2$) adsorption isotherm at a temperature of 77 K, is between 0.145 $cm^3 \cdot g^{-1}$ and 0.350 $cm^3 \cdot g^{-1}$, better still between 0.155 $cm^3 \cdot g^{-1}$ and 0.350 $cm^3 \cdot g^{-1}$, preferably between 0.165 $cm^3 \cdot g^{-1}$ and 0.350 $cm^3 \cdot g^{-1}$, better still between 0.175 $cm^3 \cdot g^{-1}$ and 0.350 $cm^3 \cdot g^{-1}$, and more preferably between 0.205 $cm^3 \cdot g^{-1}$ and 0.320 $cm^3 \cdot g^{-1}$. Said micropore volume measurement is calculated after degassing under vacuum (P<6.7×10$^{-4}$ Pa), at a temperature of between 300° C. and 450° C. for a time ranging from 9 hours to 16 hours, for example at 400° C. for 10 hours.

The process according to the invention preferably uses a zeolite adsorbent in the form of agglomerates, i.e. it comprises mesoporous crystals of at least one zeolite Y as defined previously, said crystals having a number-mean diameter between 0.1 μm and 20 μm, preferably between 0.5 μm and 20 μm, more preferably between 0.7 μm and 10 μm, even more preferentially between 0.8 μm and 10 μm, and even more preferentially between 1 μm and 5 μm.

It was in fact observed by the Applicant that the zeolite adsorbents according to the invention prepared from the crystals with a large external surface area combined with (1) a population of mesopores having improved overall matter transfer relative to that of adsorbents prepared from crystals of conventional zeolite(s) of Y type, including when said crystals are larger than the conventional crystals.

The present invention thus allows the provision of an improved process for separating meta-xylene relative to the prior art while at the same time overcoming the problems associated with the filtration, manipulation and agglomeration of submicron zeolite powders during the process for manufacturing the adsorbent.

The external surface area of the crystals contained in the adsorbent of the process described above is calculated via the t-plot method from the nitrogen adsorption isotherm at a temperature of 77 K, after degassing under vacuum (P<6.7×10$^{-4}$ Pa), at a temperature of between 300° C. and 450° C. for a time ranging from 9 hours to 16 hours, preferably at 400° C. for 10 hours.

The zeolite Y crystals with a large external surface area may be obtained according to various methods known to those skilled in the art, for example according to the synthesis described in CN 103214003.

It is also possible to prepare said crystals by synthesis by seeding and/or by adjusting the synthetic operating conditions such as the $SiO_2/Al_2O_3$ ratio, the sodium content and the alkalinity of the synthetic mixture or alternatively according to conventional processes for post-treatment of zeolite Y crystals which are known to those skilled in the art.

The post-treatment processes generally consist in removing atoms from the already-formed zeolite network, either via one or more acidic treatments which dealuminate the solid, treatment(s) followed by one or more washes with sodium hydroxide so as to remove the aluminum residues formed, as described, for example, by D. Verboekend et al., in *Adv. Funct. Mater.*, 22, (2012), 916-928, or alternatively via treatments which combine the action of an acid and that of a structuring agent which improve the efficiency of the acidic treatment, as described, for example, in patent application WO 2013/106 816.

The processes for the direct synthesis of these zeolites (i.e. synthetic processes other than the post-treatment) are preferred and generally involve one or more structuring agents or sacrificial templates. Thus, and according to yet another subject, the present invention relates to a process for separating isomers as defined previously, in which the zeolite crystals of the zeolite adsorbent are prepared by direct synthesis using one or more structuring agents or sacrificial templates.

The sacrificial templates that may be used may be of any type known to those skilled in the art and especially those described in patent application WO 2007/043 731. According to a preferred embodiment, the sacrificial template is advantageously chosen from organosilanes and more preferentially from [3-(trimethoxysilyl)propyl]-octadecyldimethylammonium chloride, [3-(trimethoxysilyl)propyl]hexadecyldimethylammonium chloride, [3-(trimethoxysilyl)propyl]dodecyldimethylammonium chloride, [3-(trimethoxysilyl)propyl]octylammonium chloride, N-[3-(trimethoxysilyl)propyl]aniline, 3-[2-(2-aminoethylamino)-ethylamino]propyltrimethoxysilane, N-[3-(trimethoxysilyl)propyl]-N'-(4-vinylbenzypethylenediamine, triethoxy-3-(2-imidazolin-1-yl)propylsilane, 1-[3-(trimethoxysilyl)propyl]urea, N-[3-(trimethoxysilyppropyl]ethylenediamine, [3-(diethylamino)-propyl]trimethoxysilane, (3-glycidyloxypropyl)trimethoxysilane, 3-(trimethoxysilyl) propyl methacrylate, [2-(cyclohexenypethyl]-triethoxysilane, dodecyltriethoxysilane, hexadecyltrimethoxysilane, (3-aminopropyl)trimethoxysilane, (3-mercaptopropyl)trimethoxysilane and (3-chloropropyl)trimethoxysilane, and also mixtures of two or more thereof in all proportions.

Among the sacrificial templates listed above, [3-(trimethoxysilyppropyl]octadecyldimethylammonium chloride, or TPOAC, is most particularly preferred.

Use may also be made of sacrificial templates of higher molar mass, for example PDAP (polydiallyldimethylammonium polymer), PVB (polyvinyl butyral) and other oligomeric compounds known in the field for increasing the diameter of mesopores.

The size of the zeolite Y crystals of the adsorbent in the process according to the invention is measured by observation with a scanning electron microscope (SEM). As indicated previously, preferably, the number-mean diameter of the crystals is between 0.1 μm and 20 μm, preferably between 0.5 μm and 20 μm, more preferably between 0.7 μm and 10 μm, even more preferentially between 0.8 μm and 10 μm and even more preferentially between 1 μm and 5 μm.

This SEM observation also makes it possible to confirm the presence of non-zeolite phase comprising, for example, residual binder (not converted during the zeolitization step) or any other amorphous phase in the adsorbents.

In the present document, the term "number-mean diameter" or "size" is used especially for the zeolite crystals. The method for measuring these magnitudes is explained later in the description.

The proportions of agglomeration binder (see the definition later) and of zeolite used in the adsorbent of the process according to the invention are typically those of the prior art, i.e. from 5 parts to 20 parts by weight of binder per 95 parts to 80 parts by weight of zeolite. The adsorbent, whether in the form of beads, extrudates or the like, preferably has a volume-mean diameter, or a length (largest dimension when it is not spherical), of between 0.2 mm and 2 mm, in particular between 0.2 mm and 0.8 mm and preferably between 0.4 mm and 0.65 mm.

The binder included in the agglomerated zeolite material of the process of the present invention comprises, and preferably consists of, a clay or a mixture of clays. These clays are preferably chosen from kaolins, kaolinites, nacrites, dickites, halloysites, attapulgites, sepiolites, montmorillonites, bentonites, illites and metakaolins, and also mixtures of two or more thereof in all proportions. Kaolin is preferred and is most commonly used.

Among the additives that may be used during the manufacture of the adsorbent of the process according to the invention, there may be a source of silica of any type known to a person skilled in the art, who is a specialist in zeolite synthesis, for example colloidal silica, diatomaceous earths, perlite, fly ash, sand or any other form of solid silica.

In the context of the present invention, the mechanical strength is measured by the Shell method series SMS 1471-74 adapted to agglomerates smaller than 1.6 mm in size. This mechanical strength, measured for the zeolite adsorbent defined previously, is generally between 1.5 MPa and 4 MPa, preferably between 1.7 MPa and 4 MPa, more preferably between 1.8 MPa and 4 MPa and most preferably between 2 MPa and 4 MPa.

During the manufacture of the adsorbent of the process according to the invention, besides the crystals of zeolite Y and the binder, other additives may also be added, for example additives for facilitating the agglomeration or for improving the hardening of the agglomerates formed, such as lignin, starch, carboxymethylcellulose and other additives known to those skilled in the art.

During the manufacture of the adsorbent of the process according to the invention, the zeolitization of the agglomeration binder may be performed according to any method that is now well known to those skilled in the art, and may be performed, for example, by immersing the product derived from the agglomeration step into an alkaline basic solution, which is generally aqueous, for example an aqueous sodium hydroxide and/or potassium hydroxide solution.

As a general rule, the concentration of the alkaline zeolitization solution is preferably between 0.5 M and 5 M. The zeolitization is preferably performed at elevated temperature, at a temperature above room temperature, and typically at temperatures of the order of 80° C. to 100° C., for example between room temperature (i.e. about 20° C.) and the boiling point of the alkaline zeolitization solution. The duration of the zeolitization process is generally between a few tens of minutes and a few hours, preferably between about 1 hour and 8 hours.

The optional step of cation exchange of the sodium ions for lithium ions may be performed according to the conventional methods known to those skilled in the art, and usually by placing the agglomerates obtained from the agglomeration step in contact with a lithium salt, such as lithium chloride (LiCl), in aqueous solution at a temperature between room temperature and 100° C. and preferably between 80° C. and 100° C.

As indicated previously, when the adsorbent comprises a zeolite NaLiY, it is also possible to agglomerate crystals of zeolite Y already containing sodium and lithium ions (partial pre-exchange of the cations present in the starting zeolite of Y type, typically sodium cations, for lithium ions).

The Applicant has observed, surprisingly, that the cation exchange step, which may be difficult on account of the relative fragility of the structure of the zeolite crystals, does not affect the intrinsic properties of external surface area and of micropore volume (relative to the mass of the adsorbent once exchanged) of said zeolite crystals.

After the cation exchange step(s), washing is then performed, generally and preferably with water, followed by drying of the agglomerate thus obtained.

The activation which follows the drying is performed in a conventional manner, according to the methods known to those skilled in the art, for example at a temperature generally between 100° C. and 400° C., preferably between 200° C. and 300° C., for a time determined as a function of the desired water content and loss on ignition, typically from 1 to 6 hours.

The invention relates to a process for separating meta-xylene from aromatic isomer fractions containing 8 carbon atoms, using as meta-xylene adsorption agent a zeolite adsorbent comprising at least one FAU-type zeolite Y as defined previously, said process being performed in liquid phase, or in gaseous phase.

The desired product (meta-xylene) may thus be separated out by preparative adsorption liquid chromatography (batchwise), and advantageously continuously on a simulated moving bed, i.e. in simulated counter-current or simulated co-current mode, and more particularly in simulated counter-current mode.

The operating conditions of an industrial simulated counter-current adsorption unit are generally the following:
  number of beds: 6 to 30,
  number of zones: at least 4 operating zones, each being located between a feed point and a withdrawal point,
  temperature between 100° C. and 250° C., preferably between 120° C. and 190° C.,
  pressure of the industrial unit between the bubble pressure of xylenes at the process temperature and 3 MPa,
  desorbent/feedstock flow rate ratio between 0.7 and 6.0,
  recycling rate between 2.0 and 20, preferably between 2.5 and 10.

Reference may be made in this respect to the teaching of patents FR 2 889 698 and FR 2 889 699.

The desorption solvent may be any desorbent known to those skilled in the art and whose boiling point is below that of the feedstock, such as toluene or indane, but also a desorbent whose boiling point is above that of the feedstock, such as tetralin. The selectivity of the adsorbents used in the process according to the invention for the adsorption of the meta-xylene contained in aromatic C8 fractions is optimal when their loss on ignition, measured at 950° C., is preferably less than or equal to 7%, preferably between 0 and 6.0%, very preferably between 0 and 4.0% and more preferably between 0 and 3.0%.

The meta-xylene separation process according to the present invention uses agglomerated zeolite adsorbents simultaneously having the characteristics of the conventional zeolite adsorbents known in the meta-xylene separation processes of the prior art, especially the mechanical and microporosity properties, the overall matter transfer characteristics being maximized relative to conventional crystal-based zeolite adsorbents.

The examples that follow illustrate the subject matter of the invention, and are given merely as a guide, without, however, being intended to limit in any way the various embodiments of the present invention.

In the examples that follow, the physical properties of the agglomerates are evaluated via the methods known to those skilled in the art, the main ones of which are recalled below:

Characterization Techniques

Particle Size of the Zeolite Crystals—Mesopore Detection

Estimation of the number-mean diameter of the Y-type zeolite crystals contained in the adsorbents used in the process according to the invention is performed by observation using a scanning electron microscope (SEM).

In order to estimate the size of the zeolite crystals on the samples, a set of images is taken at a magnification of at least 5000. The diameter of at least 200 crystals is then measured using dedicated software. The accuracy is of the order of 3%.

As indicated in U.S. Pat. No. 7,785,563, TEM also makes it possible to check whether the zeolite crystals contained in the adsorbent are filled (i.e. non-mesoporous) zeolite crystals or aggregates of filled zeolite crystals or mesoporous crystals (cf. the comparison of the TEM images of FIG. 2a and of FIG. 2b, in which the mesoporosity is clearly visible, and FIG. 3a and FIG. 3b which show filled crystals). TEM observation thus makes it possible to visualize the presence or absence of the mesopores). Preferably, the adsorbents of the process according to the invention very predominantly, i.e. typically more than 80% and preferably more than 90% by number, contain mesoporous zeolite crystals rather than filled crystals. This statistical analysis is advantageously performed by analysis of at least 50 TEM or SEM images (SEM on sections of samples obtained by ionic polishing).

Chemical Analysis of the Zeolite Adsorbents

Si/Al Ratio and Degree of Exchange

Chemical elemental analysis of the zeolite adsorbent of the process according to the invention may be performed via various analytical techniques known to those skilled in the art. Among these techniques, mention may be made of the technique of chemical analysis by x-ray fluorescence as described in standard NF EN ISO 12677 on a wavelength dispersive spectrometer (WDXRF) such as the Brüker Tiger S8 machine, or via alternative conventional methods such as methods by atomic absorption spectrometry (AAS) and inductively coupled plasma atomic emission spectrometry (ICP-AES) described in standards NF EN ISO 21587-3 or NF EN ISO 21079-3, for instance on a Perkin-Elmer 4300 DV machine.

The x-ray fluorescence spectrum has the advantage of depending very little on the chemical combination of the element, which offers a precise quantitative and qualitative determination. After calibration for each oxide $SiO_2$ and $Al_2O_3$, and also sodium oxide, a measurement uncertainty of less than 0.4% by weight is conventionally obtained. The ICP-AES method is particularly suitable for measuring the lithium content, which makes it possible to calculate the lithium oxide content.

These chemical elemental analyses make it possible both to check the Si/Al atomic ratio of the zeolite used in the preparation of the adsorbent, and the Si/Al atomic ratio of the adsorbent, and to check the quality of the ion exchange. In the description of the present invention, the measurement uncertainty of the Si/Al atomic ratio is ±5%.

The degree of exchange of the sodium ions with lithium ions is estimated by evaluating the ratio between the number of moles of lithium oxide, $Li_2O$, and the number of moles of the combination ($Li_2O+Na_2O$). It should be noted that the contents of the various oxides are given as weight percentages relative to the total weight of the anhydrous zeolite adsorbent.

Particle Size of the Zeolite Adsorbents

Determination of the volume-mean diameter of the zeolite adsorbents of the process according to the invention is performed by particle size distribution analysis of a sample of agglomerate by imaging according to standard ISO 13322-2: 2006, using a conveyor belt for conveying the sample before the objective lens of the camera.

The volume-mean diameter is then calculated from the particle size distribution by applying standard ISO 9276-2: 2001. In the present document, the term "volume-mean diameter" or "size" is used for the zeolite agglomerates. The accuracy is of the order of 0.01 mm for the size range of agglomerates of the process according to the invention.

Mechanical Strength of the Zeolite Adsorbents

The crushing strength of a bed of zeolite adsorbents as described in the present invention is characterized according to the Shell method series SMS1471-74 (Determination of bulk crushing strength of catalysts. Compression-sieve method), combined with the "BCS tester" machine sold by the company Vinci Technologies. This method, initially intended for the characterization of catalysts of 3 mm to 6 mm, is based on the use of a 425 µm screen which especially allows the fines created during crushing to be separated out. The use of a 425 µm screen remains suitable for particles with a diameter greater than 1.6 mm, but must be adapted according to the particle size of the agglomerates that it is desired to characterize.

The adsorbents of the process according to the present invention, generally in the form of beads or extrudates, generally have a volume-mean diameter or a length, i.e. the largest dimension in the case of non-spherical agglomerates, of between 0.2 mm and 2 mm, in particular between 0.2 mm and 0.8 mm and preferably between 0.4 mm and 0.65 mm. Consequently, a 100 µm screen is used in place of the 425 µm screen mentioned in Shell method series SMS1471-74.

The measurement protocol is as follows: a sample of 200 $cm^3$ of adsorbents, prescreened with the appropriate screen (100 µm) and predried in an oven for at least 2 hours at 250° C. (instead of the 300° C. mentioned in the standard Shell method SMS1471-74), is placed in a metal cylinder of known internal cross section. An increasing force is imposed in stages on this sample by means of a piston, through a bed of 5 $cm^3$ of steel balls so as to better distribute the force exerted by the piston on the agglomerates (use of balls 2 mm in diameter for particles of spherical shape with a diameter strictly less than 1.6 mm). The fines obtained at the various pressures stages are separated by screening (appropriate 100 µm screen) and weighed.

The bulk crushing strength is determined by the pressure in megapascals (MPa) for which the amount of cumulative fines passing through the screen amounts to 0.5% by weight of the sample. This value is obtained by plotting on a graph the mass of fines obtained as a function of the force applied to the bed of adsorbent and by interpolating to 0.5% by mass of cumulative fines. The mechanical bulk crushing strength is typically between a few hundred kPa and several tens of MPa and generally between 0.3 MPa and 3.2 MPa. The accuracy is conventionally less than 0.1 MPa.

Mass Amount of Zeolite Fractions in the Zeolite Adsorbents

The mass amount of zeolite fractions is measured by x-ray diffraction analysis, known to those skilled in the art by the abbreviation XRD. This analysis is performed on a Brüker machine, and the amount of zeolite fractions is then evaluated using the TOPAS software from the company Brüker.

Micropore Volume, External Surface Area and Mesopore Diameter

The crystallinity of the agglomerates is also evaluated by measuring their micropore volume and comparing it to that of a suitable reference (100% crystalline zeolite under identical cationic treatment conditions or theoretical zeolite). This micropore volume is determined from measurement of the adsorption isotherm of a gas, such as nitrogen, at its liquefaction temperature.

Prior to the adsorption, the zeolite adsorbent is degassed at between 300° C. and 450° C. for a time of between 9 hours and 16 hours, under vacuum ($P<6.7\times10^{-4}$ Pa). Measurement of the nitrogen adsorption isotherm at 77 K is then performed on a machine such as the ASAP 2020 M machine from Micromeritics, taking at least 35 measurement points at relative pressure ratios $P/P_0$ of between 0.002 and 1.

The micropore volume and the external surface area are determined from the isotherm obtained, via the t-plot method by applying standard ISO 15901-3:2007 and by calculating the statistical thickness t by means of the Harkins-Jura equation. The micropore volume and the external surface area are obtained by linear regression on the points of the t-plot between 0.45 nm and 0.57 nm, respectively, from the y-axis to the origin and from the slope of the linear regression. The evaluated micropore volume is expressed in $cm^3$ of liquid adsorbate per gram of anhydrous adsorbent. The external surface area is expressed in $m^2$ per gram of anhydrous adsorbent.

Interpretation of the nitrogen adsorption isotherm at 77 K via the Barrett-Joyner-Halenda method (BJH method, proposed in 1951) also makes it possible to obtain the pore size distribution, and especially the mesopore distribution. The volume-based mesopore size distribution is represented on the curve cN/dDm as a function of the mean pore diameter Dm.

The full width at half maximum of the volume distribution dV/dDm is given by the difference between the two mean diameters for which the value dV/dDm is equal to half of its maximum value $f_{max}$, at the top of the peak. These two mean diameters are obtained by interpolation between the desired points on either side of the mode, for which dV/dDm encompasses the value $f_{max}/2$. This full width at half maximum (FWHM) of a distribution f(x) of maximum value $f_{max}$ is illustrated schematically by way of example in FIG. 1.

Macropore and Mesopore Volume

The macropore and mesopore volumes are measured by mercury intrusion porosimetry. An Autopore® 9500 mercury porosimeter from Micromeritics is used to analyze the distribution of the pore volume contained in the macropores and in the mesopores.

The experimental method, described in the machine's operating manual, referring to standard ASTM D 4284-83, consists in placing a preweighed sample of adsorbent (granular zeolite material to be measured) (of known loss on ignition) in a porosimeter cell and then, after preliminary degassing (evacuation pressure of 30 µmHg for at least 10 minutes), in filling the cell with mercury at a given pressure (0.0036 MPa), and then in applying a pressure increasing in stages up to 400 MPa so as to make the mercury gradually penetrate into the pore network of the sample.

The relationship between the applied pressure and the apparent pore diameter is established by assuming cylindrical pores, a contact angle between the mercury and the wall of the pores of 140° and a mercury surface tension of 485 dynes/cm. The cumulative amount of mercury introduced as a function of the applied pressure is recorded. The value at and above which the mercury fills all the inter-granular voids is set at 0.2 MPa, and it is considered that above this value, the mercury penetrates into the pores of the granular material. The grain volume (Vg) is then calculated by subtracting the cumulative volume of mercury at this pressure (0.2 MPa) from the volume of the porosimeter cell, and by dividing this difference by the mass of the anhydrous equivalent granular material, i.e. the mass of said material corrected for the loss on ignition.

The macropore volume of the granular material is defined as being the cumulative volume of mercury introduced at a pressure of between 0.2 MPa and 30 MPa, corresponding to the volume contained in the pores with an apparent diameter of greater than 50 nm. The mesopore volume of the granular material is defined as being the cumulative volume of mercury introduced at a pressure of between 30 MPa and 400 MPa.

In the present document, the macropore and mesopore volumes of the zeolite adsorbents, expressed in $cm^3 \cdot g^{-1}$, are thus measured by mercury intrusion and related to the mass of the sample as anhydrous equivalent, i.e. the mass of said material corrected for the loss on ignition.

Loss on Ignition of the Zeolite Adsorbents

The loss on ignition is determined under an oxidative atmosphere, by calcination of the sample in air at a temperature of 950° C.±25° C., as described in standard NF EN 196-2 (April 2006). The measurement standard deviation is less than 0.1%.

Characterization of the Liquid-Phase Breakthrough Adsorption

The technique used for characterizing the adsorption of molecules in liquid phase on a porous solid is the technique known as breakthrough, described by Ruthven in "*Principles of Adsorption and Adsorption Processes*" (John Wiley & Sons (1984), chapters 8 and 9) which defines the breakthrough curve technique as the study of the response to the injection of a range of absorbable constituents.

Analysis of the mean exit time (first moment) of the breakthrough curves provides information regarding the amounts adsorbed and also makes it possible to evaluate the selectivities, i.e. the separation factor, between two absorbable constituents. Injection of a non-adsorbable constituent used as tracer is recommended for estimating the non-selective volumes. Analysis of the dispersion (second moment) of the breakthrough curves makes it possible to evaluate the equivalent height of theoretical plates, based on the representation of a column by a finite number of ideally stirred hypothetical reactors (theoretical stages), which is a direct measurement of the axial dispersion and of the resistance to matter transfer of the system.

EXAMPLE 1: SYNTHESIS OF ZEOLITE Y WITH A LARGE EXTERNAL SURFACE AREA

Zeolite Y with a large external surface area is synthesized directly.

Step 1): Preparation of the Growth Gel in a Stirred Reactor

A growth gel is prepared in a 3-liter stainless-steel reactor equipped with a heating jacket, a temperature probe and a stirrer, by mixing an aluminate solution containing 1146 g of Ludox AM silica sol containing 30% silica in an aluminate solution containing 198 g of sodium hydroxide (NaOH), 138 g of alumina trihydrate ($Al_2O_3 \cdot 3H_2O$, containing 65.2% by weight of $Al_2O_3$) and 800 g of water at 25° C. for 25 minutes with a stirring speed of 300 rpm.

The stoichiometry of the growth gel is as follows: $2.75Na_2O/Al_2O_3/8.20SiO_2/120H_2O$. Homogenization of the growth gel is performed with stirring at 300 rpm for 40 minutes at 25° C.

Step 2): Introduction of the Nucleation Gel into the Reaction Medium 153 g of a nucleation gel (12 $Na_2O$, $Al_2O_3$, 10 $SiO_2$, 180 $H_2O$ matured for 1 hour at 40° C.) are introduced into the reaction medium; after 5 minutes of homogenization at 300 rpm, the stirring speed is lowered to 100 rpm for 30 minutes.

Step 3): Introduction of the Structuring Agent 87.5 g of a solution of TPOAC at 60% in methanol are added at a stirring speed of 300 rpm (TPOAC/$Al_2O_3$ mole ratio=0.12). After 1 hour of homogenization, the stirring speed is lowered to 100 rpm.

Step 4): Maturation Phase

The reaction medium is kept stirring at 100 rpm at 25° C. for 17 hours, and crystallization is then started.

Step 5): Crystallization

The stirring speed is maintained at 100 rpm and the nominal temperature of the reactor jacket is set at 108° C. so that the reaction medium rises in temperature to 98° C. over 80 minutes. After 28 hours at the 98° C. stage, the reaction medium is cooled by circulating cold water in the jacket to stop the crystallization.

Step 6) Filtration/Washing

The solids are recovered on a sinter and then washed with deionized water to neutral pH.

Step 7): Drying/Calcination

In order to characterize the product, drying is performed in an oven at 90° C. for 8 hours; the loss on ignition of the dried product is 22% by weight.

Calcination of the dried product, which is necessary to release both the microporosity (water) and the mesoporosity by removing the structuring agent, is performed with the following temperature profile: 30 minutes of increase to 200° C., then 1 hour at a steady stage of 200° C., then 3 hours of increase to 550° C., and finally 1.5 hours at a steady stage at 550° C.

Pure zeolite Y crystals (identification via the x-ray diffraction spectrum) with a large external surface area of atomic ratio Si/Al 2.30 are obtained. The micropore volume and the external surface area, measured according to the t-plot method from the nitrogen adsorption isotherm at 77 K after degassing under vacuum at 400° C. for 10 hours, are, respectively, 0.214 $cm^3 \cdot g^{-1}$ and 115 $m^2 \cdot g^{-1}$. The number-mean diameter of the crystals is 1.3 μm.

EXAMPLE 2: PREPARATION OF MESOPOROUS ZEOLITE Y ADSORBENT

In the text hereinbelow, a mass expressed as anhydrous equivalent means a mass of product minus its loss on ignition.

A homogeneous mixture formed from 16 g of zeolite Y crystals with a large external surface area obtained in Example 1, 4 g of kaolin and also the amount of water allowing extrusion of the mixture is prepared. The loss on ignition of the paste before extrusion is 40%.

Extrudates 1.6 mm in diameter are formed. The extrudates are dried overnight in a ventilated oven at 80° C. They are then calcined for 2 hours at 550° C. under a stream of nitrogen, and then for 2 hours at 550° C. under a stream of dry decarbonated air.

The extrudates are then crushed so as to recover grains whose equivalent diameter is equal to 0.6 mm. The mechanical bulk crushing strength of the grains obtained above is 2.2 MPa.

The micropore volume and the external surface area, measured according to the t-plot method from the nitrogen adsorption isotherm at 77 K after degassing under vacuum at 400° C. for 10 hours, are, respectively, 0.170 $cm^3 \cdot g^{-1}$ and 137 $m^2 \cdot g^{-1}$. Analysis by x-ray diffraction confirms the presence of only one FAU-type zeolite Y phase.

EXAMPLE 3: (COMPARATIVE) PREPARATION OF NON-MESOPOROUS ZEOLITE Y ADSORBENT (CONVENTIONAL)

For comparative purposes for the preparation of the agglomerates, a pure commercial non-mesoporous zeolite Y is used, CBV100 sold by the company Zeolyst International, with an Si/Al atomic ratio equal to 2.6, a number-mean diameter of 0.6 μm and a micropore volume and external surface area measured according to the t-plot method from the nitrogen adsorption isotherm at 77 K after degassing under vacuum at 400° C. for 10 hours, which are, respectively, equal to 0.345 $cm^3 \cdot g^{-1}$ and 23 $m^2 \cdot g^{-1}$.

The operations of Example 2 are repeated in an identical manner, replacing the mesoporous zeolite Y with reference non-mesoporous zeolite Y (CBV 100 from Zeolyst).

The micropore volume and the external surface area, measured according to the t-plot method from the nitrogen adsorption isotherm at 77 K after degassing under vacuum at 400° C. for 10 hours, are, respectively, equal to 0.278 $cm^3 \cdot g^{-1}$ and 42 $m^2 \cdot g^{-1}$.

Figure 2A:
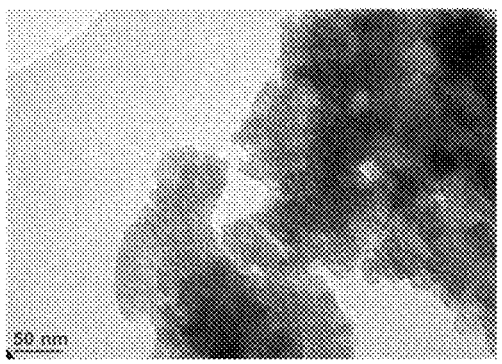
FIG. 2: (a) and (b): transmission electron microscope (TEM) image of agglomerates produced in Example 2.
Figure 2B:
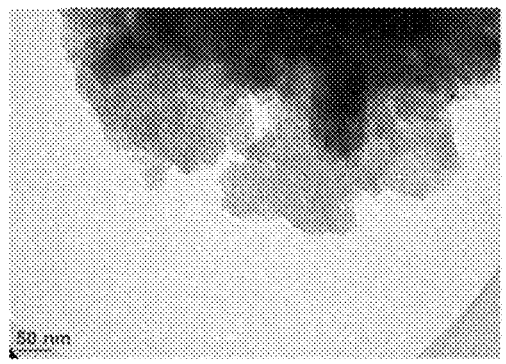
Figure 3A:
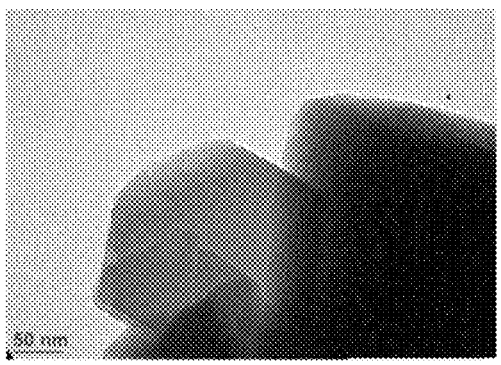
FIG. 3: (a) and (b): transmission electron microscope (TEM) image of agglomerates produced in Example 3.
Figure 3B:
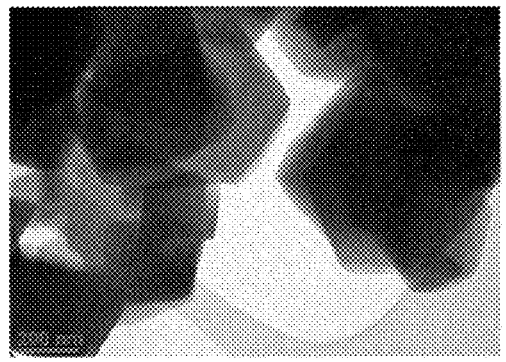

Observation with a transmission electron microscope TEM (FIGS. 2a and 2b, TEM of the agglomerates according to Example 2) and FIGS. 3a and 3b of the conventional agglomerates prepared in Example 3 reveals the presence of cavities of nanometric size (mesopores) in the agglomerates according to the invention of Example 2 (FIGS. 2a and 2b).

Figure 4:
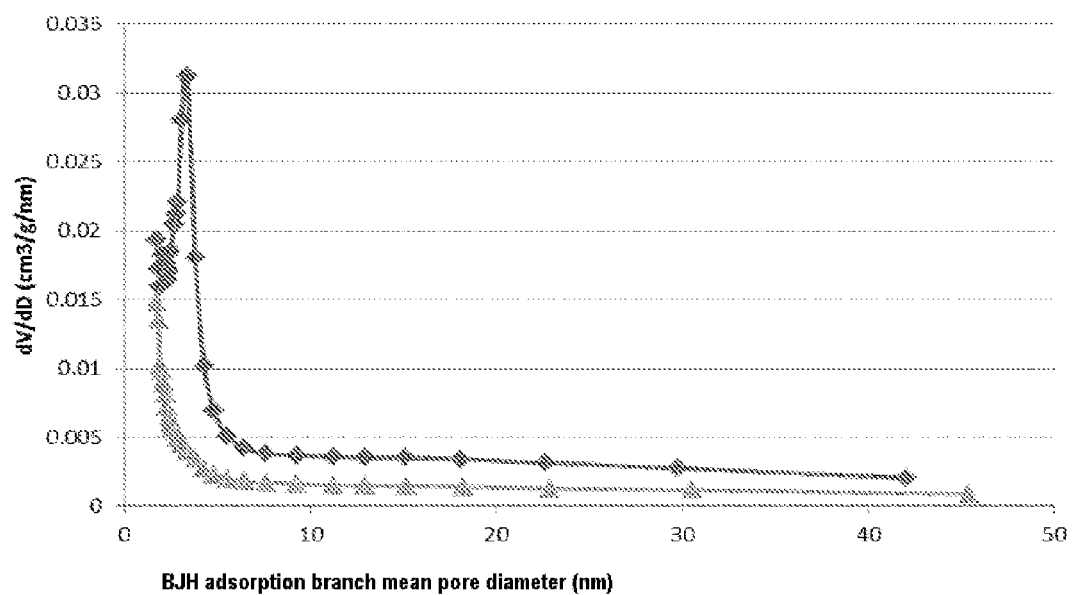
FIG. 4: comparison of the distributions of pores sizes as determined by the BJH method.

Comparison of the distributions of the pore sizes determined by the BJH method, from the nitrogen adsorption isotherm at 77 K and illustrated by FIG. 4 which clearly shows that the agglomerates according to the invention have a narrow unimodal pore size distribution in the mesopore range (i.e. pores with a mean diameter of between 2 nm and 50 nm) centered on 3.4 nm and a full width at half maximum of 2 nm (cf. curve materialized by dark diamonds). The conventional agglomerates of non-mesoporous zeolite Y (cf. curve materialized by light triangles) does not have a unimodal distribution in the mesopore range (i.e. pores with a mean diameter of between 2 nm and 50 nm); in fact, no peak having a maximum is observed on the pore size distribution.

Table 1 below presents the characteristics of the adsorbents prepared in Examples 2 and 3.

TABLE 1

|  | Adsorbent of Example 2 (according to the invention) | Adsorbent of Example 3 (conventional) |
|---|---|---|
| Micropore volume by t-plot ($cm^3 \cdot g^{-1}$) | 0.170 | 0.278 |
| External surface area ($m^2 \cdot g^{-1}$) | 137 | 42 |
| Mesopore volume ($cm^3 \cdot g^{-1}$) | 0.268 | 0.111 |
| Mesopore diameter - Mode (nm) | 3.4 | not defined |
| dV/dD mode ($cm^3 \cdot g^{-1} \cdot nm^{-1}$) | 0.031 | not defined |
| Full width at half maximum (nm) | 2.0 | not defined |

EXAMPLE 4: BREAKTHROUGH TEST ON ADSORBENTS OF EXAMPLES 2 AND 3

A breakthrough test (frontal chromatography) is then performed on these adsorbents to evaluate their efficiency. The amount of adsorbent used for this test is about 26 g.

The procedure for obtaining the breakthrough curves is as follows:
  filling the column with the sieve and inserting it in a test bench.
  filling with the solvent at room temperature.
  gradual raising to the adsorption temperature under a stream of solvent (5 $cm^3 \cdot min^{-1}$).
  injecting solvent at 30 $cm^3 \cdot min^{-1}$ when the adsorption temperature is reached.

solvent/feedstock exchange to inject the feedstock (30 cm$^3$·min$^{-1}$).

injection of the feedstock is then maintained for a time sufficient to reach thermodynamic equilibrium (i.e. until the concentration of solvent in the effluent is zero).

collecting and analyzing the breakthrough effluent.

The solvent used is para-diethylbenzene. The composition of the feedstock is as follows:

meta-xylene: 45% by weight ortho-xylene: 45% by weight isooctane: 10% by weight (this is used as tracer for estimating the non-selective volumes and does not participate in the separation)

The test is performed with an adsorption temperature of 140° C. The pressure is sufficient for the feedstock to remain in the liquid phase, i.e. 1 MPa. The circulation surface speed (flow rate/cross section of the column) of the liquid at the test temperature is about 1.2 cm·s$^{-1}$ for all the tests.

The selectivity for meta-xylene (MX) relative to ortho-xylene (OX) ($\alpha_{MX/OX}$) is calculated from the adsorbed volumes $q_{MX}$ and $q_{OX}$ of the compounds MX and OX (the latter being determined by the material balance from analysis of the breakthrough effluent) and from the composition of the feedstock (feedstock in which the volume fraction f the compounds is $y_{MX}$ and $y_{OX}$):

$$\alpha_{MX/OX} = \frac{q_{MX}}{q_{OX}} \frac{y_{OX}}{y_{MX}}.$$

The breakthrough results are given in Table 2 below:

TABLE 2

| Adsorbent | MX/OX selectivity | Adsorption capacity (%) | EHTP MX (%) |
|---|---|---|---|
| of Example 2 (invention) | 1.70 | 11.3 | 6.7 |
| of Example 3 (comparative) | 1.83 | 13.4 | 10.0 |

Key

Adsorption capacity expressed in % (cm$^3$ of C$_8$-aromatics adsorbed per cm$^3$ of column)

EHTP=Equivalent Height of Theoretical Plates measured on meta-xylene expressed in % of column length MX=meta-Xylene; OX=ortho-Xylene It is observed that the use of the adsorbent according to the invention makes it possible to considerably reduce the equivalent height of theoretical plates measured for meta-xylene, indicating an improvement in the matter transfer.

The invention claimed is:

1. A process for separating meta-xylene from aromatic isomer fractions containing 8 carbon atoms, comprising contacting an aromatic isomer fraction containing 8 carbon atoms with a zeolite adsorbent comprising at least one faujasite-type zeolite Y comprising sodium or sodium and lithium, wherein the zeolite adsorbent has an external surface area, measured by nitrogen adsorption, of greater than 40 m$^2$·g$^{-1}$, and wherein the external surface area is associated with a population of mesopores having a mean diameter of between 2 nm and 50 nm; and meta-xylene is selectively adsorbed by the zeolite adsorbent.

2. The process of claim 1, wherein the zeolite adsorbent has an external surface area, measured by nitrogen adsorption, of greater than 50 m$^2$·g$^{-1}$.

3. The process of claim 1, wherein the zeolite a sorbent has an external surface area, measured by nitrogen adsorption, of 60 to 200 m$^2$·g$^{-1}$.

4. The process of claim 1, wherein the zeolite adsorbent has a external surface area, measured by nitrogen adsorption, of 100 to 200 m$^2$·g$^{-1}$.

5. The process of claim 1, wherein the zeolite adsorbent has an external surface area, measured by nitrogen adsorption, of 80 to 200 m$^2$·g$^{-1}$.

6. The process of claim 1, wherein the zeolite adsorbent has a pore size, as determined via the Barrett-Joyner-Halenda method from the nitrogen adsorption isotherm at 77 K, for pores between 2 nm and 50 nm, that is unimodal and narrow.

7. The process of claim 1, wherein the zeolite adsorbent is an adsorbent based on FAU-type zeolite(s) Y, wherein the zeolite adsorbent has a Si/Ai atom ratio of greater than 1.50.

8. The process of claim 1, wherein the zeolite adsorbent has a mass fraction of FAU-type zeolite(s) Y of greater than or equal to 80% relative to the total weight of the zeolite adsorbent.

9. The process of claim 1, wherein the zeolite adsorbent has a lithium content, of less than 8%, expressed as eight of lithium oxide Li$_2$O relative to the total mass of the zeolite adsorbent.

10. The process of claim 1, wherein the zeolite adsorbent simultaneously comprises pores having a diameter of greater than 50 nm, pores having a diameter of between 2 nm and 50 nm, limits not included, and pores having a diameter of less than 2 nm.

11. The process of claim 1, wherein the zeolite adsorbent has macropores and micropores and wherein the zeolite adsorbent has a total volume contained in the macropores and the mesopores (sum of the macropore volume and of the mesopore volume) measured by mercury intrusion, of between 0.20 cm$^3$·g$^{-1}$ and 0.70 cm$^3$·g$^{-1}$.

12. The process of claim 1, wherein the zeolite adsorbent has a ratio (macropore volume)/(macropore volume+mesopore volume) of between 0.2 and 1.

13. The process of claim 1, wherein the zeolite adsorbent has a micropore volume, evaluated by the t-plot method from the nitrogen (N$_2$) adsorption isotherm at a temperature of 77 K, of between 0.145 cm$^3$·g$^{-1}$ and 0.350 cm$^3$·g$^{-1}$.

14. The process of claim 1, wherein the zeolite adsorbent comprises mesoporous crystals of at least one zeolite Y, wherein the mesoporous crystals have a number-mean diameter of between 0.1 μm and 20 μm.

15. The process of claim 1, wherein the zeolite adsorbent contains zeolite crystals and wherein the zeolite crystals are prepared by direct synthesis using one or more structuring agents or sacrificial templates.

16. The process of claim 1, wherein the meta-xylene is separated by preparative adsorption liquid chromatography.

17. The process of claim 1, wherein the zeolite adsorbent is an adsorbent based on FAU-type zeolite(s) Y, wherein the zeolite adsorbent has a Si/Al atomic ratio between 1.50 and 6.50.

18. The process of claim 1, wherein the zeolite adsorbent has a lithium content of between 0 and 4%, expressed as weight of lithium oxide Li$_2$O relative to the total mass of the zeolite adsorbent.

19. The process of claim 1, wherein the zeolite adsorbent containing macropores and micropores and wherein the zeolite adsorbent has a total volume contained in the macropores and the mesopores (sum of the macropore volume and of the mesopore volume) measured by mercury intrusion, of between 0.20 cm$^3$·g$^{-1}$ and 0.50 cm$^3$·g$^{-1}$.

20. The process of claim 1, wherein the zeolite adsorbent has a ratio (macropore volume)/(macropore volume+mesopore volume) of between 0.4 and 0.8.

21. The process of claim 1, wherein the zeolite adsorbent has a micropore volume, evaluated by the t-plot method from the nitrogen ($N_2$) adsorption isotherm at a temperature of 77 K, of between 0.205 cm$^3$·g$^{-1}$ and 0.320 cm$^3$·g$^{-1}$.

22. The process of claim 1, wherein the zeolite adsorbent comprises mesoporous crystals of at least one zeolite Y, wherein the crystals have a number-mean diameter of between 0.7 μm and 10 μm.

23. The process of claim 1, which is conducted in a liquid phase or a gas phase.

24. The process of claim 1, which is conducted in a counter-current adsorption unit.

25. The process of claim 24, wherein the counter-current adsorption unit (a) has 6 to 30 beds, (b) has at least four operating zones, (c) is operated at a temperature between 100 C and 250 C, (d) a desorbent/feedstock flow rate ratio between 0.7 and 6.0, and (e) a recycling rate between 2.0 and 20.

26. The process of claim 1, further comprising contacting the zeolite adsorbent with a desorption solvent.

* * * * *